United States Patent
Conley et al.

(10) Patent No.: US 8,639,337 B2
(45) Date of Patent: *Jan. 28, 2014

(54) PACEMAKER PASSIVE MEASUREMENT TESTING SYSTEM

(75) Inventors: Vickie L. Conley, Woodbury, MN (US); James O. Gilkerson, Stillwater, MN (US); David L. Perschbacher, Coon Rapids, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 135 days.

This patent is subject to a terminal disclaimer.

(21) Appl. No.: 13/273,098

(22) Filed: Oct. 13, 2011

(65) Prior Publication Data

US 2012/0029589 A1 Feb. 2, 2012

Related U.S. Application Data

(63) Continuation of application No. 12/765,486, filed on Apr. 22, 2010, now Pat. No. 8,046,071, which is a continuation of application No. 11/559,456, filed on Nov. 14, 2006, now Pat. No. 7,729,765, which is a continuation of application No. 11/010,974, filed on Dec. 13, 2004, now Pat. No. 7,149,580, which is a continuation of application No. 10/118,601, filed on Apr. 8, 2002, now Pat. No. 6,845,269, which is a continuation of application No. 09/378,315, filed on Aug. 20, 1999, now Pat. No. 6,370,432.

(51) Int. Cl.
*A61N 1/37* (2006.01)

(52) U.S. Cl.
USPC ............................................. 607/28; 607/27

(58) Field of Classification Search
None
See application file for complete search history.

(56) References Cited

U.S. PATENT DOCUMENTS

| | | | |
|---|---|---|---|
| 4,142,533 | A | 3/1979 | Brownlee et al. |
| 4,332,256 | A | 6/1982 | Brownlee et al. |
| 4,390,020 | A | 6/1983 | Herpers et al. |
| 4,445,512 | A | 5/1984 | Krupka et al. |
| 4,503,858 | A | 3/1985 | Markowitz et al. |
| 4,527,568 | A | 7/1985 | Rickards |
| 4,556,063 | A | 12/1985 | Thompson et al. |
| 4,585,004 | A | 4/1986 | Brownlee |
| 4,596,255 | A | 6/1986 | Snell et al. |
| 4,791,936 | A | 12/1988 | Snell et al. |

(Continued)

FOREIGN PATENT DOCUMENTS

EP 0715866 12/1995

OTHER PUBLICATIONS

"U.S. Appl. No. 09/378,315, First Office Action mailed Apr. 5, 2001", 7 pgs.

(Continued)

*Primary Examiner* — Kennedy Schaetzle
(74) *Attorney, Agent, or Firm* — Schwegman Lundberg & Woessner, P.A.

(57) ABSTRACT

A system and method for passively testing a cardiac pacemaker in which sensing signal amplitudes and lead impedance values are measured and stored while the pacemaker is functioning in its programmed mode. The amplitude and impedance data may be gotten and stored periodically at regular intervals to generate a historical record for diagnostic purposes. Sensing signal amplitudes may also be measured and stored from a sensing channel which is currently not programmed to be active as long as the pacemaker is physically configured to support the sensing channel. Such data can be useful in evaluating whether a switch in the pacemaker's operating mode is desirable.

20 Claims, 3 Drawing Sheets

(56) References Cited

U.S. PATENT DOCUMENTS

| | | |
|---|---|---|
| 4,809,697 A | 3/1989 | Causey, III et al. |
| 4,830,005 A | 5/1989 | Woskow |
| 4,899,750 A | 2/1990 | Ekwall |
| 4,920,969 A | 5/1990 | Suzuki et al. |
| 4,979,506 A | 12/1990 | Silvian |
| 5,007,427 A | 4/1991 | Suzuki et al. |
| 5,111,818 A | 5/1992 | Suzuki et al. |
| 5,312,445 A | 5/1994 | Nappholz et al. |
| 5,369,364 A | 11/1994 | Renirie et al. |
| 5,406,955 A | 4/1995 | Bledsoe et al. |
| 5,423,325 A | 6/1995 | Burton |
| 5,431,161 A | 7/1995 | Ryals et al. |
| 5,431,692 A | 7/1995 | Hansen et al. |
| 5,453,698 A | 9/1995 | Williams et al. |
| 5,476,485 A | 12/1995 | Weinberg et al. |
| 5,503,159 A | 4/1996 | Burton |
| 5,534,018 A | 7/1996 | Wahlstrand et al. |
| 5,549,646 A | 8/1996 | Katz et al. |
| 5,553,623 A | 9/1996 | Ochs |
| 5,662,690 A | 9/1997 | Cole et al. |
| 5,722,405 A | 3/1998 | Goldberg |
| 5,741,311 A | 4/1998 | McVenes et al. |
| 5,755,742 A | 5/1998 | Schuelke et al. |
| 5,803,914 A | 9/1998 | Ryals et al. |
| 5,873,894 A | 2/1999 | Vandegriff et al. |
| 5,891,178 A | 4/1999 | Mann et al. |
| 6,370,432 B1 | 4/2002 | Conley et al. |
| 6,845,269 B2 | 1/2005 | Conley et al. |
| 7,149,580 B2 | 12/2006 | Conley et al. |
| 7,729,765 B2 | 6/2010 | Conley et al. |
| 2002/0177881 A1 | 11/2002 | Conley et al. |
| 2005/0102004 A1 | 5/2005 | Conley et al. |
| 2007/0073349 A1 | 3/2007 | Conley et al. |
| 2010/0204746 A1 | 8/2010 | Conley et al. |

OTHER PUBLICATIONS

"U.S. Appl. No. 09/378,315, Notice of Allowance mailed Oct. 24, 2001", 3 pgs.

"U.S. Appl. No. 09/378,315, Response filed Jul. 5, 2001 to First Office Action mailed Apr. 5, 2001", 7 pgs.

"U.S. Appl. No. 10/118,601, Final Office Action mailed Jun. 23, 2004", 4 pgs.

"U.S. Appl. No. 10/118,601, Notice of Allowance mailed Sep. 10, 2004", 6 pgs.

"U.S. Appl. No. 10/118,601, Preliminary Amendment filed Jul. 8, 2002", 7 pgs.

"U.S. Appl. No. 10/118,601, Response filed Aug. 23, 2004 to Final Office Action mailed Jun. 23, 2004", 10 pgs.

"U.S. Appl. No. 11/010,974, Notice of Allowance mailed Aug. 1, 2006", 9 pgs.

"U.S. Appl. No. 11/559,456, Notice of Allowance mailed Jan. 19, 2010", 10 pgs.

"U.S. Appl. No. 12/765,486, Non Final Office Action mailed Jan. 19, 2011", 7 pgs.

"U.S. Appl. No. 12/765,486, Notice of Allowance mailed Jun. 24, 2011", 5 pgs.

"U.S. Appl. No. 12/765,486, Response filed Apr. 13, 2011 to Non Final Office Action mailed Jan. 19, 2011", 8 pgs.

PACEMAKER PASSIVE MEASUREMENT TESTING SYSTEM

CLAIM OF PRIORITY

This patent application is a continuation of U.S. application Ser. No. 12/765,486, filed on Apr. 22, 2010, now issued as U.S. Pat. No. 8,046,071, which is a continuation of U.S. application Ser. No. 11/559,456, filed on Nov. 14, 2006, now issued as U.S. Pat. No. 7,729,765, which is a continuation of U.S. Application Ser. No. 11/010,974, filed on Dec. 13, 2004, now issued as U.S. Pat. No. 7,149,580, which is a continuation of U.S. patent application Ser. No. 10/118,601, filed Apr. 8, 2002, now issued as U.S. Pat. No. 6,845,269, which is a continuation of U.S. patent application Ser. No. 09/378,315, filed on Aug. 20, 1999, now issued as U.S. Pat. No. 6,370,432, the specification of which is incorporated herein by reference.

FIELD OF THE INVENTION

This invention pertains generally to the field of cardiac pacemakers and implantable cardioverter-defibrillators having a pacemaking function. In particular, the invention relates to a system and method for testing selected operating parameters in an implanted pacemaker.

BACKGROUND

As pacemaker technology has developed, a number of standard operating modes have been developed which define how the device paces the heart. These modes are usually described by a three-letter code developed by the Inter-Society Commission for Heart Disease where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive and designated by a fourth letter added to the three-letter code, R.

Modern pacemakers also typically have the capability to communicate data via a radio-frequency link with an external programming device. Such data is transmitted to the pacemaker in order to program its mode of operation as well as define other operating parameters. Data transmitted from the pacemaker can be used to verify the operating parameters as well as relay information regarding the condition of both the pacemaker and the patient. Pacemaker patients are monitored at regular intervals as part of routine patient care and to check the condition of the device. Among the data which may typically be telemetered from the pacemaker are its programming parameters, an electrogram representing the electrical activity of the heart as sensed by the pacemaker, and electrical operating characteristics such as battery voltage, signal amplitude, and lead impedance.

Pacemakers have also been developed which monitor certain parameters over time while the device is functioning in the patient. Data representing these parameters can be stored in memory for later retrieval using an external programmer. Such parametric data may include the impedance of a lead that is attached to a patient's heart and the internal impedance of a battery used to power the device. In addition, the data measurements may be taken passively so as to be synchronized with the occurrence of a cardiac event, such as using a spontaneous depolarization to measure signal amplitude from a sensing channel. Similarly, the application of a stimulation pulse by the pacemaker to the patient's heart allows measurement of a lead impedance by measuring the current flowing through the lead when the voltage pulse of known magnitude is applied. The parametric data may be measured and stored at predetermined time intervals, as indicated by a clock within the device. Such storage of data allows the observation of trends in the data as well as detection of changes which may only occur intermittently.

Telemetry of certain types of data between the external programmer and the pacemaker can take place while the pacemaker is functioning in its currently programmed mode. Others cannot, however, because to do so might affect the operation of the pacemaker. In order to program the pacemaker, for example, it must first be put in a default pacing mode in which it can safely pace the patient while the programming parameters are adjusted. Depending upon the patient, this would typically be an asynchronous ventricular pacing mode (VOO). Other types of data which in prior art devices cannot be transmitted from the pacemaker while functioning in its programmed mode include those which derive from the pacemaker operating in a currently unprogrammed mode such as sensing signals from sensing channels not used in the current mode. Simply turning on an unused sensing channel has the potential to disturb the pacing function of the pacemaker since its programming will not allow the new incoming signal to be properly interpreted.

SUMMARY OF THE INVENTION

The present invention is directed toward a system and method which allows a pacemaker to be tested with passive measurements taken while the pacemaker is functioning in its currently programmed mode. (The term "pacemaker" as used herein should be taken to mean both pacemakers and any device with a pacemaking function, such as an implantable cardioverter/defibrillator with a pacemaker incorporated therein.) In contrast with prior art devices, such measurements may include signal amplitude values taken from channels which are inactive or not being used in the current operating mode. Such data may be useful to the clinician in ascertaining whether the device is capable of operating in another mode in a particular patient. In particular, the invention allows the atrial and ventricular sensing channels of a programmable pacemaker to be passively tested while the pacemaker is operating in mode where either of the sensing channels is inactive.

In accordance with the invention, a passive measurement testing mode is activated which causes a pacemaker functioning in a particular programmed mode to measure and store certain parameter values as the pacemaker transitions to test states corresponding to programmed operating states allowing such measurements to take place. In the case of parameter values not currently derivable from the current operating mode, such as the signal amplitude from a currently unprogrammed sensing channel, a virtual sensing test state corresponding to the unprogrammed channel may be interposed into the operation of the device where the pacemaker then operates as if programmed in a mode including that sensing state. The virtual sensing test state is transitioned to upon receipt of a sensing signal in the corresponding sensing channel after the expiration of any programmed refractory periods. During the virtual sensing test state an amplitude value corresponding to the sense signal is stored in memory, and no inhibition or triggering of pacing pulses is effected. The virtual sensing test state returns to the state from which it was entered.

Also in accordance with the invention, a lead impedance measuring test state may cause lead impedance values to be measured and stored when the pacemaker enters a pacing state, corresponding to the occurrence of an event which triggers output of a pacing pulse through the lead to be measured to a heart chamber according to the pacemaker's programmed mode. An impedance value of the lead through which the pacing pulse is delivered can then be measured during output of the pacing pulse and stored in memory. In the event that no pacing pulse occurs for a given lead, either because the patient's intrinsic rhythm during the test state is enough to inhibit pacing or because the pacemaker is not currently programmed to pace through the lead, a virtual pacing test state may be interposed into the pacemaker's operation. During such state, which is entered upon receipt of a sense signal from a heart chamber connected to the lead to be measured, a measuring pulse is output during the chamber's refractory period allowing the impedance of the lead to be measured and stored.

DETAILED DESCRIPTION OF THE INVENTION

The basic function of a modern pacemaker is to deliver pacing pulses to the heart in accordance with sensed cardiac signals. Programmability of the pacemaker allows it to operate in a number of different pacing modes. The electronic circuitry for controlling the pacemaker can be either in the form of custom integrated circuits or a microprocessor based design with application specific software. Because of its inherent flexibility and the ease with which additional functionality can be added, a microprocessor-based designs is the most widely used. In the description that follows, a microprocessor-based pacemaker will be referred to as incorporating the system and method which is the present invention. It should be appreciated, however, the invention could also be incorporated into a pacemaker controlled by custom logic circuitry either in addition to or instead of a programmed microprocessor. The term "circuitry" as used herein should therefore be taken to mean either custom circuitry or a microprocessor executing programmed instructions contained in a processor-readable storage medium along with associated circuit elements.

Figure 1:
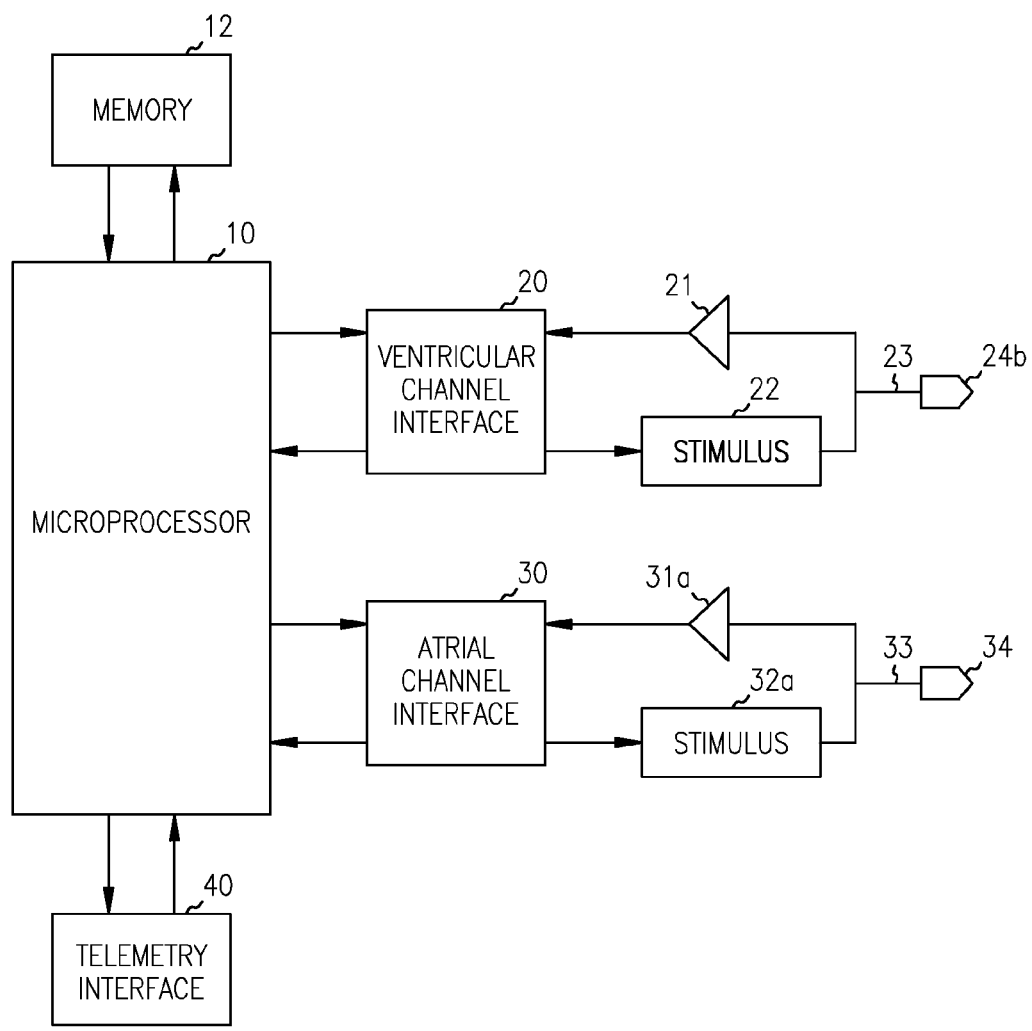
FIG. 1 is a system diagram of a microprocessor-based dual chamber pacemaker.

FIG. 1 shows a system diagram of a microprocessor-based dual-chamber pacemaker. A microprocessor 10 communicates with a memory 12 via a bidirectional data bus. The memory 12 typically comprises a ROM for program storage and a RAM for data storage. The microprocessor also has a port for communicating with the telemetry interface 40 which in turn receives programming data from and transmits telemetry data to an external programmer by a radio link. The pacemaker also has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The channel interfaces 20 and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

A cardiac pacemaker is basically a device that responds to sensed cardiac events and elapsed time intervals by changing its functional states so as to deliver pacing pulses to the heart at appropriate times and properly interpret sensed data. As such, the essential operation of a pacemaker can be usefully represented from a state machine perspective. A state machine is a computational device which transitions from one state to another based on a defined set of rules unique to each state regarding inputs and timer events. In the following description, the operation of a pacemaker incorporating the present invention is described as such a state machine. It should be realized, however, that this description refers to the external behavior of the device and not to any specific implementation by either the programming of the microprocessor or discrete logic circuitry.

Figure 2:
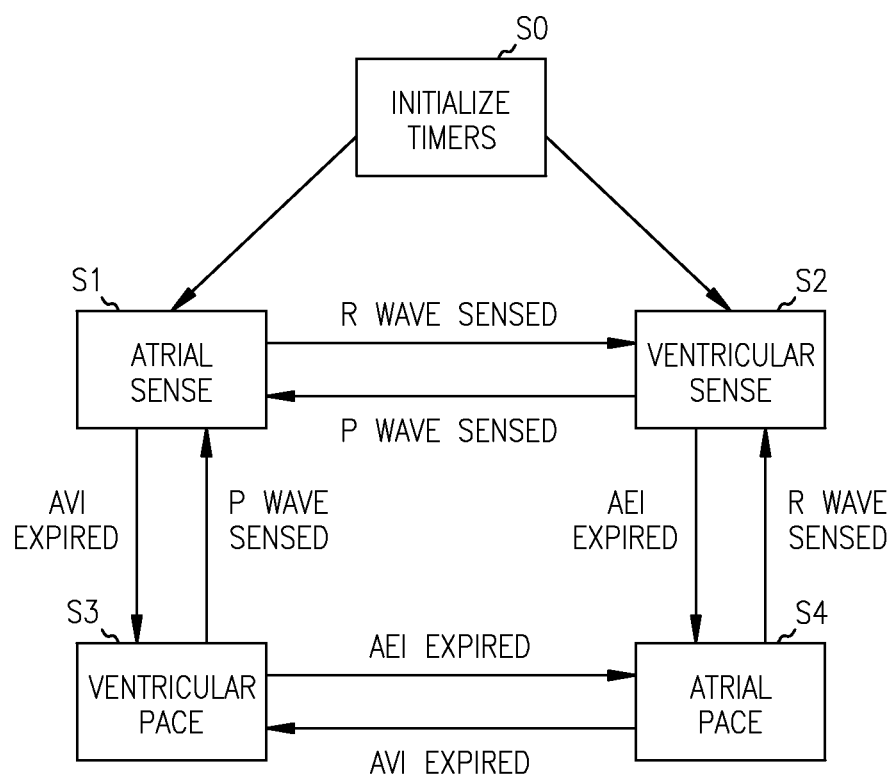
FIG. 2 is a state machine diagram showing the operation of a pacemaker in DDD mode.

FIG. 2 shows a state machine representation of a simplified pacemaker operating in DDD mode which has five basic states: state S0 where interval timers are initialized, state S1 indicating a ventricular sense, state S2 indicating an atrial sense, state S3 to pace the ventricle, and state S4 to pace the atrium. The system moves from state to state based upon sensed events and the outputs of timers for two intervals: AEI for atrial escape interval which defines the minimum rate at which the atria will be paced in the absence of spontaneous activity, and AVI for atrioventricular interval which defines a minimum time interval in which a spontaneous ventricular depolarization must occur following an atrial sense or pace. If the AVI expires following an atrial sense or pace, a ventricular pace is delivered. Not shown are other time intervals used to define refractory periods for the sensing channels during which time the channels are closed so that inputs are ignored. (The term "refractory" means a no sensing condition when applied to a sensing channel, to be distinguished from the physiological refractory period of excitable tissue.) Sensing channels are rendered refractory both in order to prevent reentry into the system of an output pacing pulse (in which case the sensing amplifiers are blanked) and to prevent the misinterpretation of input data by the sensing of after potentials or by crosstalk between sensing channels. An actual DDD pacemaker may even use additional algorithms for interpreting input data, but it must still exhibit the functionality defined by FIG. 1

If it is desired to perform passive testing in the device of FIG. 2 in order to store a record of sense signal amplitudes and lead impedances, test states can be added to the operation of the pacemaker which allows the testing and recording to be done while the pacemaker is operating in its programmed mode. The non-test states of the device will be referred to a programmed states. In order to test a programmed sensing or pacing channel passively, there must be a corresponding test state for each such channel to be tested. For example, one test state is an amplitude storing state for storing signal amplitudes which is entered upon detection that a corresponding programmed sensing state has been entered due to receipt of a signal from a sensing channel which is not in its refractory period. Another test state is a lead impedance measuring state which is entered after detecting that the pacemaker has entered a corresponding pacing state due to the occurrence of an event which triggers output of a pacing pulse according to the programmed mode. The lead impedance measuring state measures an impedance value of the lead through which the pacing pulse is delivered during output of the pacing pulse and stores the value in a memory. A test state has the same transition rules as its corresponding programmed state so that the programmed operation of the device is undisturbed by the passive testing.

Figure 3:
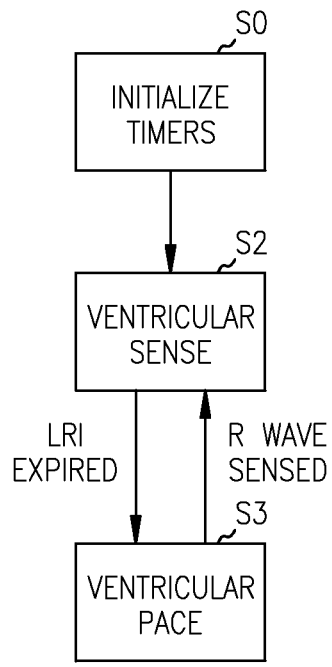
FIG. 3 is a state machine diagram showing the operation of a pacemaker in VVI mode.

FIG. 3 shows a state machine diagram of a pacemaker operating in VVI mode which has three basic states: state S0 for initialization, state S1 indicating a ventricular sense, and state S3 for outputting a pacing pulse to the ventricle. The system moves from state to state based upon sensed ventricular events (i.e., R waves) and the output of a lower rate interval (LRI) timer that defines a minimum rate at which the ventricles will be paced in the absence of spontaneous activity. The ventricular sense signal amplitude and ventricular lead impedance can be measured passively with testing states as described above. If the VVI pacemaker is a dual-chamber one having the capability of operating in DDD mode and physically configured with an atrial lead and sensing channel, it would be desirable to be able to passively measure atrial signal amplitude as well. Simply turning on the atrial sense amplifier (which may be turned off when the pacemaker is in VVI mode to conserve power) with an amplitude storing state is not enough because the operation of the pacemaker does not include an atrial sensing state in its current programming. This means that there are no transition rules that define how an atrial sensing state should be entered and exited. Nor does the pacemaker have an atrial channel refractory period timer which is needed in order not to misinterpret a ventricular depolarization or a pacing pulse as an atrial sense signal.

Figure 4:
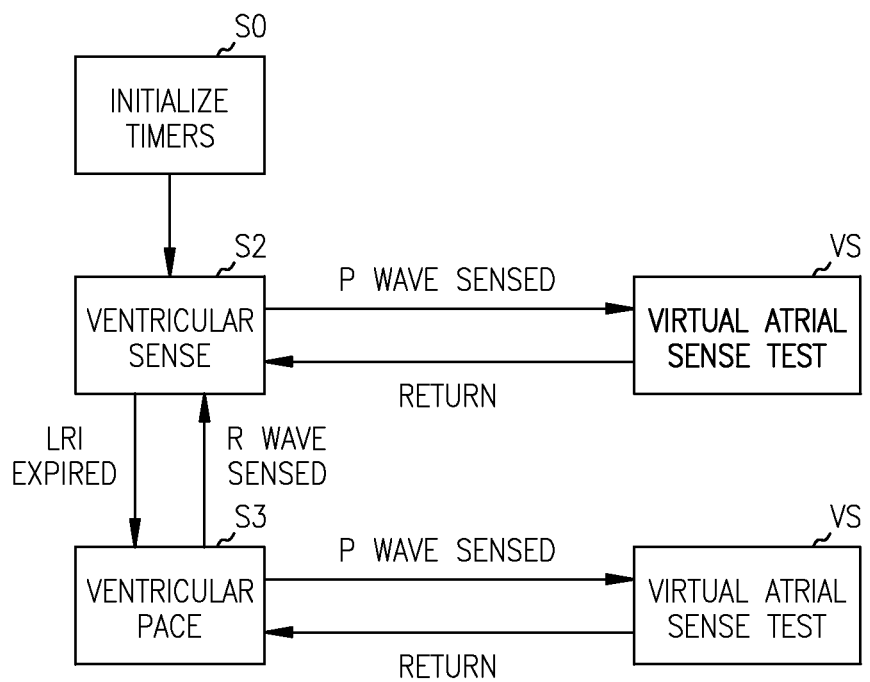
FIG. 4 is a state machine diagram showing the operation of a pacemaker operating in VVI mode with the capability of passively testing an unprogrammed sensing channel.

FIG. 4 shows a state transition diagram of a pacemaker incorporating a testing system in accordance with the present invention. A virtual sensing test state VS corresponding to the currently unprogrammed sensing channel (i.e., the atrial channel in this case) is added to the operation of the pacemaker where the pacemaker then operates as if programmed in a mode including that sensing state. The virtual sensing test state includes a refractory period timer in its transition logic in order to properly interpret sensing signals. The virtual testing state is thus transitioned to upon receipt of a sensing signal in the corresponding sensing channel, and an amplitude value corresponding to the sense signal is stored in memory. The term "virtual" in this context means that transition to the virtual sensing state results in no triggering or inhibition of pacing pulses as would be the case were the pacemaker simply programmed to operate with the atrial sensing channel active. The transition rule of the virtual sensing test state is to return to the state from which the virtual state was entered in order to leave the programmed operation of the device undisturbed.

The testing states as described may be part of a passive measurement testing mode which when activated causes the testing states to persist until signal amplitudes and lead impedances for all available channels are stored. The microprocessor is thus programmed to maintain the testing mode until all testing has been performed and then deactivate the testing mode. An amplitude test interval timer can be used to set a limit on the time for which the system will wait for a sensing signal to store. Upon expiration of the interval, the system aborts the test sequence. Similarly, a lead test interval timer can be used to limit the time the system waits for a pacing pulse to occur through a lead in order to measure its impedance. Upon expiration of that interval, however, instead of aborting the lead impedance test, a virtual pacing test state may be employed where "virtual pacing" in this context means the outputting of a pacing pulse to the chamber to which the lead is connected occurs shortly after a depolarization during the chamber's refractory period. The impedance of the lead can then be measured and stored. Similarly, a virtual pacing state may be used to measure the impedance of a shock lead in the case of an implantable cardioverter-defibrillator.

The passive measurement testing mode as described can be initiated either by a telemetry command from an external programmer or by a timer which causes periodic testing at regular intervals in order to store a record of historical values. For example, the passive measurement testing mode can be set to activate once per day and store a week's worth of signal amplitude and lead impedance values. An average taken over a selected number of most recent values can also be calculated and stored for later retrieval.

The system and method as described above may be used in situations where it is desired to evaluate operating parameters of an implanted pacemaker which are not currently derivable in its current operating mode. Such nonprogrammed parameters may be useful in planning a switch of operating modes. For example, atrial triggering modes such as DDD or VDD are desirable in chronotropically competent patients in need of ventricular pacing because they allow the pacing to track the physiologically normal atrial rhythm. Atrial triggering modes are contraindicated, however, in patients prone to atrial fibrillation or flutter or in whom a reliable atrial sense cannot be obtained. In the former case, the ventricles will be paced at too high a rate. Failing to sense an atrial P wave, on the other hand, results in a loss of atrial tracking which can lead to negative hemodynamic effects. This is because the pacemaker then reverts to its minimum ventricular pacing rate after failing to sense the P wave, and the next P waves may occur so early that they fall within the post-ventricular refractory period of the atrial channel. The minimum rate pacing may thus continue for several cardiac cycles until a P wave is again sensed. For such patients, a synchronous non-atrial triggered mode such as VVI or DVI set at an appropriate minimum rate is usually best. It may be the case, however, that with proper adjustment of parameters, such as amplifier gain and signal threshold, reliable atrial sensing could actually be accomplished. If it can be determined that such parameter adjustments are successful, the patient can be switched to the more desirable atrial triggered mode. The present invention allows periodic samples of atrial sensing signals to be taken and stored over time even while the pacemaker is operating in VVI, DVI, or any other non-atrial sensing mode. The atrial sensing data can then be used to decide if the atrial sensing is reliable enough to allow switching the patient to an atrial triggered mode.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac pacemaker having a plurality of sensing channels each including a lead for coupling to a heart having an atrial region and a ventricular region, the pacemaker comprising:
a controller programmed to:
operate the pacemaker in a first mode during which a first channel of the plurality of sensing channels is programmed to be an inactive channel, the first mode having a plurality of states;
activate a passive measurement testing mode;
receive a sensing signal from the inactive channel;
transition from a current state of the plurality of states to a test state in response to the sensing signal being received after the passive measurement testing mode is activated;
measure one or more parameter values using the inactive channel during the test state; and
return to the current state after the one or more parameter values are measured.

2. The pacemaker of claim 1, further comprising a storage medium, wherein the controller is programmed to store the measured one or more parameter values and return to the current state after the measured one or more parameter values are stored.

3. The pacemaker of claim 1, wherein the controller is programmed to deactivate the passive measurement testing mode after the one or more parameter values are measured.

4. The pacemaker of claim 3, further comprising a telemetry interface, and wherein the controller is programmed to activate the passive measurement testing mode in response to receiving a command via the telemetry interface.

5. The pacemaker of claim 3, wherein the controller is programmed to activate the passive measurement testing mode on a periodic basis.

6. The pacemaker of claim 5, wherein the controller is programmed to activate the passive measurement testing mode once per day.

7. The pacemaker of claim 1, wherein the controller is programmed to measure an amplitude value associated with the sensing signal during the passive measurement testing mode.

8. The pacemaker of claim 1, wherein the controller is programmed to measure a first lead impedance value associated with the lead of the inactive channel during the passive measurement testing mode.

9. The pacemaker of claim 8, wherein the controller is programmed to measure a second lead impedance value associated with a second channel of the plurality of sensing channels, the second channel programmed to be an active channel.

10. The pacemaker of claim 1, wherein the controller is programmed to switch to operating the pacemaker in a second mode during which the first channel is programmed to become an active channel in response to the first channel being determined to be reliable for sensing based on the one or more parameter values measured during the passive measurement testing mode.

11. The pacemaker of claim 10, wherein the first channel is an atrial channel adapted to be coupled to the atrial region through the lead of the first channel.

12. The pacemaker of claim 11, wherein the controller is programmed to:
determine whether atrial sensing is reliable using the measured one or more parameter values; and
switch to operating the cardiac pacemaker in an atrial triggered mode in response to the atrial sensing being determined to be reliable.

13. The pacemaker of claim 12, wherein the controller is programmed to switch to operating the cardiac pacemaker in a DDD or VDD mode from a non-atrial sensing mode in response to the atrial sensing being determined to be reliable.

14. The pacemaker of claim 11, wherein the controller is programmed to perform a lead impedance test during the passive measurement testing mode, the lead impedance test including:
delivering at least one atrial pacing pulse through the lead of the first channel during a refractory period of the atrial region; and
measuring an atrial lead impedance value associated with the lead of the first channel.

15. The pacemaker of claim 14, wherein a second channel of the plurality of sensing channels is a ventricular channel adapted to be coupled to the ventricular region through the lead of the second channel, and the lead impedance test further includes:
delivering at least one ventricular pacing pulse through the lead of the second channel of the plurality of sensing channels during a refractory period of the ventricular region; and
measuring a ventricular lead impedance value associated with the lead of the second channel.

16. A cardiac pacemaker having a plurality of sensing channels each including a lead for coupling to a heart, the pacemaker comprising:
means for operating the pacemaker in a first mode during which a first channel of the plurality of sensing channels is programmed to be an inactive channel, the first mode having a plurality of programmed states;
means for initiating a passive measurement testing mode;
means for transitioning from a current state of the plurality of states to a test state in response to receipt of a sensing signal from the inactive channel after the passive measurement testing mode is initiated;
means for measuring one or more parameter values using the inactive channel during the test state; and
means for returning to the current state after the one or more parameter values are measured.

17. The pacemaker of claim 16, further comprising means for storing the measured one or more parameter values.

18. The pacemaker of claim 17, wherein the means for initiating the passive measurement testing mode comprises means for activating the passive measurement testing mode on a periodic basis.

19. The pacemaker of claim 17, wherein the means for measuring the one or more parameter values comprises means for measuring an amplitude value associated with the sensing signal.

20. The pacemaker of claim 19, wherein the means for measuring one or more parameter values comprises means for measuring impedance values associated with the leads of the plurality of sensing channels.

* * * * *